(12) United States Patent
Domke et al.

(10) Patent No.: US 9,194,845 B2
(45) Date of Patent: *Nov. 24, 2015

(54) DEVICE FOR OUTPUTTING AND/OR RECEIVING ULTRASOUND AND ULTRASOUND SENSOR FOR INSPECTING A VALUABLE DOCUMENT

(75) Inventors: Jan Domke, Vaterstetten (DE); Joseph Lohner, München (DE); Hans-Uwe Moosler, München (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 509 days.

This patent is subject to a terminal disclaimer.

(21) Appl. No.: 13/541,130

(22) Filed: Jul. 3, 2012

(65) Prior Publication Data

US 2012/0266678 A1  Oct. 25, 2012

Related U.S. Application Data

(63) Continuation of application No. 12/520,765, filed as application No. PCT/EP2007/011208 on Dec. 19, 2007, now Pat. No. 8,230,742.

(30) Foreign Application Priority Data

Dec. 22, 2006 (DE) .......................... 10 2006 061 337

(51) Int. Cl.
*G01N 29/04* (2006.01)
*G01N 29/34* (2006.01)
(Continued)

(52) U.S. Cl.
CPC .............. *G01N 29/348* (2013.01); *G01N 29/11* (2013.01); *G07D 7/08* (2013.01); *G01N 2291/0237* (2013.01)

(58) Field of Classification Search
CPC .......... G01N 29/11; G01N 2291/0237; G01N 29/348; G07D 7/08
USPC ........... 73/642, 632, 623, 625, 626, 628, 629; 310/334–336
See application file for complete search history.

(56) References Cited

U.S. PATENT DOCUMENTS 4,174,636 A    11/1979  Pagano
4,523,122 A     6/1985  Tone et al.
(Continued)

FOREIGN PATENT DOCUMENTS

CN          2391234 Y      8/2000
DE          4323134 C1     6/1994
(Continued)

OTHER PUBLICATIONS

Klyuev, V.V., "Unangreifbare Steuerung und Diagnostik", Moscow, publishing house "Masinostroenie", 1995, p. 154. (partial English translation thereof).

(Continued)

*Primary Examiner* — J M Saint Surin
(74) *Attorney, Agent, or Firm* — Workman Nydeger (57) ABSTRACT

An apparatus for emitting and/or receiving ultrasound in a predetermined frequency range includes at least one ultrasonic converter for converting ultrasound into electrical signals and/or converting electrical signals into ultrasound, and a holder having at least one ultrasonic channel formed therein in which the ultrasonic converter is disposed at least partly and/or through which ultrasound can pass from or to the ultrasonic converter. The holder has at least one non-fibrous surface layer adjacent to at least one portion of the ultrasonic channel, whose impedance is smaller than that of an inside layer of the holder neighboring to the surface layer.

19 Claims, 6 Drawing Sheets

(51) Int. Cl.
*G01N 29/11* (2006.01)
*G07D 7/08* (2006.01)

(56) References Cited

U.S. PATENT DOCUMENTS

| | | | |
|---|---|---|---|
| 4,526,077 A | 7/1985 | DeGuvera | |
| 4,576,048 A | 3/1986 | Glenn | |
| 4,612,807 A | 9/1986 | Wunderer | |
| 5,115,414 A | 5/1992 | Atalar et al. | |
| 5,121,628 A | 6/1992 | Merkl et al. | |
| 5,661,243 A | 8/1997 | Bryan et al. | |
| 5,681,996 A | 10/1997 | White | |
| 6,134,967 A | 10/2000 | White | |
| 6,252,967 B1 | 6/2001 | Moore et al. | |
| 6,314,054 B1 | 11/2001 | Priebsch | |
| 6,407,964 B1 | 6/2002 | Hornung et al. | |
| 6,598,529 B2 * | 7/2003 | Muller | 101/484 |
| 6,825,594 B1 | 11/2004 | Thurn | |
| 7,242,796 B2 | 7/2007 | Matsui et al. | |
| 7,912,272 B2 | 3/2011 | Joshi et al. | |
| 7,987,717 B2 * | 8/2011 | Casagrande et al. | 73/573 |
| 8,570,622 B2 * | 10/2013 | Pellaton et al. | 358/498 |
| 2003/0025512 A1 | 2/2003 | Wunderer | |
| 2007/0187209 A1 | 8/2007 | Stenzel et al. | |
| 2013/0069299 A1 * | 3/2013 | Matsuoka et al. | 271/10.01 |

FOREIGN PATENT DOCUMENTS

| | | |
|---|---|---|
| DE | 19844447 | 3/2000 |
| DE | 19921217 | 11/2000 |
| DE | 19957125 A1 | 6/2001 |
| EP | 0167010 A2 | 1/1986 |
| EP | 0740154 | 10/1996 |
| GB | 615684 | 1/1949 |
| JP | 4315910 | 11/1992 |
| WO | 2005013207 A1 | 2/2005 |

OTHER PUBLICATIONS

Search Report of German Patent and Trademark Office regarding German Patent Application No. 10 2006 061 337.6, Sep. 21, 2007.

* cited by examiner

DEVICE FOR OUTPUTTING AND/OR RECEIVING ULTRASOUND AND ULTRASOUND SENSOR FOR INSPECTING A VALUABLE DOCUMENT

CROSS REFERENCE TO RELATED APPLICATION

This application is a continuation application of Ser. No. 12/520,765, filed Dec. 30, 2009, which is the national stage entry of PCT/EP2007/011208 filed on Dec. 19, 2007, which claims priority to the German application DE 10 2006 061 337.6, filed Dec. 22, 2006, the entirety of all of said applications being incorporated herein by reference.

FIELD OF INVENTION

The present invention relates to an apparatus for emitting and/or receiving ultrasound, in particular for examining a value document, and to an ultrasonic sensor for examining a value document.

BACKGROUND

Value documents are understood here to be sheet-shaped objects that represent for example a monetary value or an authorization and are hence not to be producible at will by unauthorized persons. Hence, they have features that are not easily produced, in particular copied, whose presence is an indication of authenticity, i.e. production by an authorized body. Important examples of such value documents are chip cards, coupons, vouchers, checks and in particular bank notes.

Such value documents are in many cases to be examined by machine for their authenticity and/or their physical condition, for example, limpness or the presence of tears, holes or adhesive strips.

For such a check there can be used in known apparatuses for processing value documents in particular ultrasound. The corresponding apparatus then has an ultrasonic sensor which can comprise in particular an apparatus for emitting and/or receiving ultrasound. In such examinations, ultrasound can either be emitted continuously or in pulsed fashion onto a value document and the ultrasound thrown back by the value document or preferably the ultrasound passed through the value document be detected; then the corresponding detection signals are evaluated.

Such an ultrasonic sensor can also be used in value document processing apparatuses wherein stacks of value documents are singled, for determining singling errors, in particular the substantially simultaneous removal of two at least partly superposed value documents, also referred to as double or multiple removal.

If the principal direction of propagation or the mean direction of propagation of the ultrasound extends at least approximately orthogonal to the surface of the value document, however, there can occur the undesirable effect that the value document throws the ultrasound back in the direction of an ultrasonic converter used in the ultrasonic sensor. Upon use of continuously emitted ultrasound this, and optionally reflection on the ultrasonic sensor, can result in standing waves which falsify the examination. If the ultrasound is emitted only in the form of pulses, a pulse can be reflected as a so-called pulse echo and likewise impair the examination.

SUMMARY

The present invention is hence based on the object of providing an apparatus for emitting and/or receiving ultrasound, in particular for examining a value document, or an ultrasonic sensor for examining a value document, which permit an examination of value documents which minimizes impairments by undesirable reflections of the employed ultrasound.

This object is achieved according to a first alternative by an apparatus for emitting and/or receiving ultrasound at least of a predetermined frequency having at least one ultrasonic converter for converting ultrasound at least of the predetermined frequency into electrical signals and/or for converting electrical signals into ultrasound at least of the predetermined frequency, and a holder having formed therein at least one ultrasonic channel in which the ultrasonic converter is disposed at least partly and/or through which ultrasound can pass from or to the ultrasonic converter, the holder having at least one non-fibrous surface layer adjacent to at least one portion of the ultrasonic channel and whose impedance is smaller than that of an inside layer of the holder neighboring to the surface layer, in particular adjacent thereto.

The inventive apparatus is used for emitting and/or receiving ultrasound of at least one frequency which is predetermined. Preferably, in particular for operation with short ultrasonic pulses, the apparatus can also be configured for ultrasonic conversion in a predetermined frequency range which contains the predetermined frequency. For pulsed operation the width of the frequency range can conform inter alia to the desired pulse duration. The predetermined frequency or the frequency range is preferably within the frequency range of 100 kHz to 1 MHz, particularly preferably between 100 kHz and 600 kHz, for applications in the area of processing and/or checking value documents. For applications in the area of processing and/or checking value documents by means of ultrasonic pulses, the width of the frequency range can be chosen for example smaller than 70 kHz. The conversion of electrical signals into ultrasound with the predetermined frequency and/or the conversion of ultrasound with the predetermined frequency into electrical signals is done using the ultrasonic converter, which is configured or chosen according to the predetermined frequency or the predetermined frequency range. There can be chosen here any, in particular known, ultrasonic converters, for example converters with a surface circular cylindrical along the circumference and radiating the ultrasound. The ultrasonic converter can have on its ultrasound-radiating surface in particular a layer connected to an actuator, for example to a piezoelectric element, specifically for coupling in ultrasound in air.

The ultrasonic converter can be disposed at least partly in the ultrasonic channel of the holder, i.e. be countersunk wholly or partly in the holder. The ultrasonic channel is then so designed that the ultrasonic converter can oscillate with the accordingly provided portions freely enough for converting ultrasound. It is also possible, however, that the ultrasonic converter is disposed in a receiving means in the holder at one end of the ultrasonic channel which opposes the end of the ultrasonic channel through which ultrasound can pass from the holder or into the holder.

The ultrasonic channel can thereby in particular also exert an influence on the spatial radiating or receiving characteristic of the apparatus for ultrasound in the predetermined frequency range and be designed accordingly.

Further, the ultrasonic converter can be disposed with its radiating direction in principle at will relative to the holder. Preferably, with a holder having a level surface facing the value document upon an examination, the ultrasonic converter and preferably the ultrasonic channel are so aligned that the radiating direction is aligned with a normal to the surface to an angle between 0° and 5°, particularly preferably between 0° and 1°.

Normally, upon acoustic irradiation of an object by a thus disposed ultrasonic converter of a conventional apparatus, at least a portion of the ultrasound is thrown back onto the ultrasonic converter, which leads in continuous operation to standing waves and in pulsed operation to multiple echoes.

Surprisingly, it has now been found that the formation of standing waves or the formation of strong multiple echoes can be substantially reduced by the holder having the at least one non-fibrous surface layer adjacent to at least one portion of the ultrasonic channel or at least partly limiting the latter, whose impedance is smaller than that of an inside layer of the holder neighboring to the surface layer, in particular adjacent thereto. A non-fibrous surface layer is understood here to be a layer made of a material not present in the form of fibers, in particular a solid state material including elastic materials or foams. Fibrous surface layers, in contrast, are textile fabrics such as so-called "nonwovens", for example felts or fleeces, or wovens, knits, etc.

The surface layer can be adjacent to the inside layer in particular in the radial direction of the ultrasonic channel, or in a direction parallel to the direction of the ultrasonic channel or the direction of sound propagation in the ultrasonic channel.

This design of the holder has the advantage that non-fibrous materials can be processed very simply and exactly, while the formation of portions of an ultrasonic channel in a fibrous material is possible only inexactly in particular in the case of small diameters.

The term "impedance" is understood in general within the scope of the present invention to be acoustic impedance. In principle it is sufficient that the impedance of the surface layer is smaller than that of the inside layer. Preferably, the impedance of the material of the surface layer is in the range between 20% and 75% of the impedance of the material of the inside layer. In this case an especially good suppression of standing waves or multiple reflections is obtained.

The density or impedance of the material of the surface layer is understood to be, in the case of inhomogeneous surface layers, the average along a normal to the surface of the surface layer through the surface layer.

The surface layer need in principle not form the entire surface limiting the ultrasonic channel. However, the surface layer preferably extends up to an end of the ultrasonic channel facing away from the ultrasonic converter. In other words, it extends up to the surface of the holder in the radiating direction or out of the entrance direction. In this manner it is also possible to reduce the reflection of ultrasound impinging on the holder immediately beside the ultrasonic channel.

In a plane transverse to the radiating direction it can likewise be sufficient that only a sector of the surface limiting the ultrasonic channel is formed by the surface layer. This can be desirable in particular when the radiating or receiving characteristic is to differ for certain spatial directions. It is preferable, however, that the surface layer encloses the portion of the ultrasonic channel at least in ring-like fashion. This makes it possible to achieve an attenuation of standing waves or multiple reflections that is better and less directional regarded in a plane transverse to the direction of radiated or received ultrasound. Furthermore, manufacturing can be simplified.

In principle the holder can be formed of one piece, the surface layer being formed by a change in the composition of the material of the holder. For example, the holder can have a layer structure. According to a first variant, however, the holder can also comprise a base body with a receiving means and a sleeve-shaped portion disposed at least partly in the receiving means, or a sleeve disposed at least partly in the receiving means, said portion or sleeve comprising the surface layer and having the ultrasonic converter disposed at least partly therein. Said portion or sleeve in which the portion of the ultrasonic channel extends can be connected to the base body in the receiving means in force-fitting and/or form-fitting and/or material-locking fashion, i.e. for example by friction or clamping and or by material-locking connection by means of a material for producing an adhesive connection.

The sleeve or sleeve-shaped portion of a suitable body can be obtained for example by processing a blank or by using a suitable mold upon production from liquid or pasty materials.

Alternatively, it is possible that the holder is formed by a base body made of the material of the surface layer, whereby material of the higher impedance is disposed around the surface layer or the receiving area in a direction transverse to the radiating direction or receiving direction.

In principle the material used for the surface layer can be any material having a suitable impedance. However, the surface layer is preferably formed from a material whose average density is at least 10% smaller than the average density of the material of the inside layer. The average density is understood here to be the normal density in the case of homogeneous materials, and in the case of inhomogeneous materials the density of areas that are much greater than the essential dimensions of the structural inhomogeneities, in the case of matrix composites for example of the areas embedded in the matrix. This has the advantage that for influencing the impedance of a material its density can be influenced more easily than the sound velocity.

In principle the density of the surface layer can be chosen at will as long as the impedance of the surface layer is smaller than that of the inside layer. It has been found that the density of the material of the surface layer is preferably between 0.3 g/cm$^3$ and 0.8 g/cm$^3$. An especially effective reduction of standing waves or multiple reflection results when the density of the surface layer assumes a value between 0.4 g/cm$^3$ and 0.7 g/cm$^3$.

The density of the inside layer is also in principle arbitrary, but is preferably in the range between 0.8 g/cm$^3$ and 1.8 g/cm$^3$.

In principle the material used for the surface layer can be a homogeneous material. However, the surface layer preferably comprises a composite material with a weight proportion of the surface layer of more than 80%. Particularly preferably, the surface layer comprises the composite material substantially, i.e. at more than 95 wt. %.

The composite material may in principle be any isotropic or anisotropic composite material. It is preferable to use a composite material wherein bodies or areas are embedded in a matrix that do not have the composition of the matrix. It is particularly preferable to use a composite material with a matrix, and bodies distributed therein in a disordered order on which a scattering and/or absorption of ultrasound at least of the predetermined frequency can be effected. This permits the occurrence of standing waves or the strength of multiple reflections to be reduced further.

It has been found that an especially good reduction of standing waves or multiple reflections is surprisingly achieved when the material of the surface layer comprises a syntactic foam and preferably consists thereof. A syntactic foam is understood to be in particular a material that comprises a matrix material with hollow bodies, preferably hollow spheres, embedded therein. The syntactic foam is preferably transmissive at least partly to the ultrasound of the predetermined frequency, so that an at least small portion can pass through the surface layer onto the inside layer. This kind of composite material can have the advantage that a scattering of the ultrasound can partly take place on the hollow bodies, which impairs its propagation.

In particular for application in the area of the checking of value documents, the syntactic foam can contain hollow bodies, in particular hollow spheres, with a diameter between 5 µm and 200 µm. In addition, the syntactic foam can also have hollow bodies of different diameter, but their proportion of the number of hollow bodies, based on the volume of the foam, is preferably smaller than 20%. Particularly preferably, the range in which the diameters of the hollow bodies lie can be the range between 5 µm and 120 µm. The diameter of one of the hollow bodies is understood here to be in particular the diameter of the smallest sphere enclosing the hollow body, i.e. in the case of hollow spheres in particular their normal diameter. The hollow bodies can be distributed monodispersely or uniformly with regard to their diameters in this range or, preferably, have a bimodal or multimodal distribution. The use of a bimodal or multimodal distribution can offer the advantage that, upon the preferred use of hollow spheres as hollow bodies, a substantially higher packing density of the hollow spheres can be obtained, which leads to reduced density and thus impedance and possibly to elevated scattering.

The hollow spheres can fundamentally be manufactured from any material. Preferably, the syntactic foam contains hollow glass spheres, preferably ones whose diameter is between 5 µm and 200 µm. The use of hollow glass spheres has the advantage that they are readily available, compared to other materials.

As the matrix material of the syntactic foam there can be used in principle any material in which the hollow bodies are embeddable. Preferably, the syntactic foam contains as the matrix material a polymeric material, particularly preferably a resin. Depending on the requirement, there can be used here for example epoxy resins or polyurethane resins.

The thickness of the surface layer can be chosen for example in dependence on the predetermined frequency and the impedance of the inside layer. In particular, the surface layer can have a thickness greater than one quarter of the wavelength in the surface layer corresponding to the predetermined frequency and smaller than 10 mm.

The inventive apparatus need not possess only one ultrasonic converter. Rather, it is preferable that the apparatus has at least one further ultrasonic converter and wherein the holder possesses at least one further ultrasonic channel in which the further ultrasonic converter is disposed at least partly, the holder having at least one further non-fibrous surface layer adjacent to at least one further portion of the further ultrasonic channel, whose impedance is smaller than that of a further inside layer of the holder adjacent to the further surface layer.

The further surface layer can preferably be configured according to at least one of the previously described embodiments.

The then at least two ultrasonic converters, the corresponding ultrasonic channels, and the corresponding surface and inside layers need not necessarily have the same properties and the same structure, but this is preferably the case.

In particular in this case, it is preferable that the surface layers are formed for at least two of the ultrasonic channels or ultrasonic converters by portions of a single molded part. This embodiment offers not one but several advantages. For example, a subsequent equipping of a base body for the holder with surface layers which are formed by sleeve-shaped portions of the molded body can be effected in only one working step.

For a simple production it can prove to be especially favorable if the holder has at least two layers, one of which is formed by the molded part in which the corresponding portions of the ultrasonic channels can be formed.

Furthermore, upon use of syntactic foams based on polymeric matrix materials, such a molded part can often be produced especially easily, without any mechanical processing being necessary.

The apparatus can preferably be used for examining value documents with ultrasound. The object is hence achieved according to the first alternative further by an ultrasonic sensor for examining value documents with at least one inventive apparatus.

In particular, it is preferable in the case of the ultrasonic sensor, for example for detecting double or multiple removals of value documents by a singler or for checking value documents, that said sensor is provided for examining value documents by means of ultrasound passing therethrough, that said sensor has at least one further inventive apparatus, and that the apparatuses are disposed relative to each other such that their holders form a, preferably slit-shaped, detection area through which a value document is transportable, and the ultrasonic converters of the apparatuses form at least one ultrasound path when one thereof is operated as a transmitter and the other thereof as a receiver. Such ultrasonic sensors permit examinations in transmission which are at the same time very robust and informative.

With such ultrasonic sensors it is advantageously possible to further reduce the formation of standing waves or the occurrence or effect of multiple reflections when, in the case of the ultrasonic sensor, the holder of the apparatus or at least of one of the apparatuses has on the surface facing the detection area or the value document upon an examination at least one non-fibrous surface layer whose impedance is smaller than that of an inside layer of the holder adjacent to the surface layer. The surface layer adjacent to the detection area in which a value document is located upon an examination or through which it is transported can be configured in particular according to one or more of the above-mentioned embodiments of the surface layer on the ultrasonic channels. Further, it can advantageously be configured as a molded part which at the same time has the sleeve-shaped portions.

The object is also achieved according to a second alternative by an ultrasonic sensor for checking a value document in a detection area of the ultrasonic sensor by means of ultrasound at least of a predetermined frequency with a first ultrasonic converter acting as a transmitter for the ultrasound and a second ultrasonic converter acting as a receiver for the ultrasound, the ultrasonic converters being so disposed that they form an ultrasound path extending through the detection area, and at least one of the ultrasonic converters having a surface portion inclined relative to the ultrasound path for radiating ultrasound and/or for receiving ultrasound.

The ultrasonic sensor according to the second alternative of the invention thus has the two ultrasonic converters one of which is configured for emitting ultrasound at least of the predetermined frequency and the other for receiving ultrasound at least of the predetermined frequency. The ultrasonic converters can otherwise be configured identically or differently.

Due to the incline of the surface portion relative to the ultrasound path, in particular a connecting line between the oscillating surfaces of the ultrasonic converters emitting or receiving the ultrasound, ultrasound is likewise emitted or received inclined to the direction the ultrasound path. Since it also holds for a reflection of ultrasound on a value document that the angle of incidence is approximately the angle of reflection, reflected portions of the ultrasound emitted by the surface portion are reflected out of the area of the ultrasound path, so that standing waves do not arise, or at least not to such an extent, or reflected pulses, in particular also multiply reflected pulses, do not impinge on one of the ultrasonic converters of the ultrasound path again, or only with very low strength. Further, portions of the ultrasound impinging on the ultrasonic converters are reflected up out of the immediate area of the ultrasound path by the inclined surface area.

Compared with a solution in which the ultrasound path is inclined to the surface of the value document to reduce the effect of reflections, there results a reduced installation space of the ultrasonic sensor.

Although it can in principle be sufficient that the surface portion is level, the surface portion of the at least one ultrasonic converter is preferably configured rotationally symmetrically around the direction of the ultrasound path. It is then either possible for a sound field similar to a sound cone to be emitted, so that upon reflection on for example a value document the sound portions more greatly inclined to the direction of the ultrasound path are directed out of the ultrasound path by reflection and can hence no longer influence the ultrasonic converters, or it is possible for portions impinging on the ultrasonic converters to be reflected away from the ultrasound path outwardly.

The surface portion can in particular be of conical or frustoconical configuration. This embodiment has the advantage that said surface portion can be produced especially easily and at the same time a very good effect results.

To also obtain a good focusing of the emitted ultrasound or an angular-dependent receiving characteristic that is not too wide, the cone opening angle of the surface portion is preferably between 160° and 176°.

To obtain a good transmitting or receiving efficiency, the surface portion preferably has a maximum external diameter that is between the wavelength in air corresponding to the frequency and ten times the wavelength in air. Air can be assumed at normal conditions according to the DIN standard or at a temperature of 20° C. at a pressure of 1 bar and a relative air humidity of 75%.

An especially small installation space results when the ultrasonic sensor has at least one transport element for guiding the value document in the detection area, and when the ultrasonic converters are so disposed that the ultrasound path forms an angle smaller than 5° with a normal to the surface of the value document. The transport element can involve for example straps or rollers or similar transport elements which determine the position of the value document relative to the ultrasonic sensor.

As mentioned above, only one of the ultrasonic converters needs to have an inclined surface portion. However, an especially good function is obtained if the other ultrasonic converter is also configured according to an embodiment or a combination of at least two of the embodiments previously mentioned in connection with the second alternative.

With such ultrasonic sensors it is advantageously possible to reduce the formation of standing waves or the occurrence or effect of multiple reflections further by providing, in the area of the ultrasonic channel through which ultrasound is radiated or received by the ultrasonic converter, an ultrasound-absorbing layer, for example made of a fibrous material, in particular felt. However, there can also be provided alternatively or additionally in the case of the ultrasonic sensor at least one element limiting the detection area and having a non-fibrous surface layer whose impedance is smaller than that of an inside layer of the element adjacent to the surface layer. The element can be configured in particular as a holder for the particular ultrasonic sensor. The surface layer adjacent to the detection area can further be configured according to one or more of the above-mentioned embodiments of the surface layer in the ultrasonic channels. Thus the impedance of the material of the surface layer is preferably in the range between 20% and 75% of the impedance of the material of the inside layer. In this case an especially good suppression of standing waves or multiple reflections is obtained.

Furthermore, said layer can advantageously be configured as a molded part which at the same time has the sleeve-shaped portions.

This embodiment has the advantage that the ultrasound impinging on the surface limiting the detection area is likewise not reflected or only reflected in a strongly attenuated form, which greatly limits the formation of standing waves or the occurrence of strong multiple reflections.

The object is achieved according to a third alternative by an ultrasonic sensor for checking a value document in a detection area of the ultrasonic sensor by means of ultrasound of a predetermined frequency having an ultrasonic converter acting as a transmitter for the ultrasound, an ultrasonic converter acting as a receiver for the ultrasound, and at least one holder for the ultrasonic converters, wherein the at least one holder limits the detection area at least partly and at least one portion, limiting the detection area, of the at least one holder has in the surroundings of the ultrasonic converter disposed in or on the holder a non-fibrous surface layer whose impedance is smaller than that of an inside layer of the holder adjacent to the surface layer.

In particular, the ultrasonic sensor can have a holder in each case for the ultrasonic converters which limit the detection area at least partly, whereby at least one portion, limiting the detection area, of the holders has in the surroundings of the ultrasonic converter disposed in or on the holder a non-fibrous surface layer whose impedance is smaller than that of an inside layer of the holder adjacent to the surface layer.

For the properties and features of the surface layer, the embodiments described with respect to the surface layer in the first alternative are likewise advantageously applicable.

Thus, it is in principle possible to use as the material for the surface layer any materials having a suitable impedance. Preferably, the surface layer is formed from a material whose average density is at least 10% smaller than the average density of the material of the inside layer. The average density is understood here to be, in the case of homogeneous materials, the normal density and, in the case of inhomogeneous materials, the density of areas that are much greater than the essential dimensions of the structural inhomogeneities, in the case of matrix composites for example the areas embedded in the matrix. This has the advantage that the density of a material can be influenced more easily than the sound velocity.

In principle, the density of the surface layer can be chosen at will as long as the impedance of the surface layer is smaller than that of the inside layer. It has been found that the density of the material of the surface layer is preferably between 0.3 g/cm$^3$ and 0.8 g/cm$^3$. An especially effective reduction of standing waves or multiple reflection results when the density of the surface layer assumes a value between 0.4 g/cm$^3$ and 0.7 g/cm$^3$.

The density of the inside layer is also in principle arbitrary, but is preferably in the range between 0.8 g/cm$^3$ and 1.8 g/cm$^3$.

In principle it is possible to use as the material of the surface layer a homogeneous material. However, the surface layer preferably comprises a composite material with a weight proportion of the surface layer of more than 80%. Particularly preferably, the surface layer comprises the composite material substantially, i.e. at more than 95 wt. %.

The composite material may in principle be any isotropic or anisotropic composite material. It is preferable to use a composite material wherein bodies or areas are embedded in a matrix that do not have the composition of the matrix.

It has been found that an especially good reduction of standing waves or multiple reflections is surprisingly achieved when the material of the surface layer comprises a syntactic foam, preferably consists thereof. A syntactic foam is understood here to be in particular a material comprising a matrix material with hollow bodies, preferably hollow spheres, embedded therein. The syntactic foam is preferably transmissive at least partly to the ultrasound of the predetermined frequency, so that an at least small portion can pass through the surface layer onto the inside layer. This kind of composite material has the advantage that a scattering of the ultrasound can partly take place on the hollow bodies, which impairs its propagation.

In particular for the application in the area of the checking of value documents, the syntactic foam can contain hollow bodies, in particular hollow spheres, with a diameter between 5 μm and 200 μm. The syntactic foam can also contain hollow bodies of different diameter, but their proportion of the number of hollow bodies, based on the volume of the foam, is then preferably smaller than 20%. Particularly preferably, the range in which the diameters of the hollow bodies lie can be the range between 5 μm and 120 μm. The diameter of one of the hollow bodies is understood here to be in particular the diameter of the smallest sphere which encloses the hollow body, in the case of hollow spheres i.e. in particular their normal diameter. The hollow bodies can be distributed monodispersely with regard to their diameters in this range or have a bimodal or multimodal distribution. The use of a bimodal or multimodal distribution can offer the advantage that, upon the preferred use of hollow spheres as hollow bodies, a substantially higher packing density of the hollow spheres is obtained.

The hollow spheres can fundamentally be manufactured from any material. Preferably, the syntactic foam contains hollow glass spheres, preferably ones whose diameter is between 5 μm and 200 μm. The use of hollow glass spheres has the advantage that they are readily available, compared to other materials.

As the matrix material of the syntactic foam there can be used in principle any materials in which the hollow bodies are embeddable. However, the syntactic foam preferably contains as the matrix material a polymeric material, particularly preferably a resin. Depending on the requirement, there can be used here for example epoxy resins or polyurethane resins.

The thickness of the surface layer can be chosen for example in dependence on the predetermined wavelength range and the impedance of the inside layer. In particular, the surface layer can have a thickness greater than one quarter of the wavelength in the surface layer corresponding to the predetermined frequency and smaller than 10 mm.

Further, the ultrasonic sensor can have at least one or a combination of at least two of the features of the ultrasonic sensor according to the first alternative. In particular, there can, in the case of the ultrasonic sensor, be formed at least in one of the holders at least one ultrasonic channel in which the particular ultrasonic converter is disposed at least partly and/or through which ultrasound can pass from or to the ultrasonic converter, the holder having at least one non-fibrous surface layer adjacent to at least one portion of the ultrasonic channel and whose impedance is smaller than that of an inside layer neighboring to the surface layer of the holder. Preferably, the material of the surface layer adjacent to the ultrasonic channel and of the surface layer limiting the detection area are identically configured, although this need not necessarily be the case.

All stated alternatives offer the advantage that two measurements can be performed at a relatively short time interval due to the strong attenuation or suppression of pulses reflected by the value document. Typically it is necessary to wait after the emission of an ultrasonic pulse intended for measurement until all echoes of the pulse, i.e. singly or multiply reflected parts of the pulse, have faded away far enough so as not to impair the detection of the transmitted measuring pulse for the next measurement. If fewer or weaker pulse echoes occur, the next measuring pulse can hence be emitted faster.

If the attenuation of a reflected pulse is very strong, the length of the ultrasound path can also be reduced, which likewise reduces the time required for measurement, which is determined by the pulse transit time, and the installation space for the particular ultrasonic sensor.

The object can further be achieved by an ultrasonic sensor for checking a value document in a detection area of the ultrasonic sensor by means of ultrasound of a predetermined frequency having an ultrasonic converter acting as a transmitter for the ultrasound and an ultrasonic converter acting as a receiver for the ultrasound, a holder portion in each case for the transmitter and the receiver which have ultrasonic channels flush with each other in each case in which the transmitter and receiver are disposed in completely countersunk fashion so as to form an ultrasound path extending through the detection area, and wherein the ultrasonic converters are disposed so as to be inclined to an axis of alignment of the ultrasonic channels.

Due to the inclined arrangement of the ultrasonic converters there is achieved a similar effect as with the ultrasonic sensor of the second alternative, whereas it is possible here to use ultrasonic converters having level, non-inclined surfaces, for example standard ultrasonic converters.

The above-described embodiments for the lining of the ultrasonic channel or the surface of a holder are advantageously applicable here too, because the laterally drifting echoes then greatly lose intensity upon each reflection.

Particularly preferably, the surfaces of the ultrasonic channels and the surface of the holder portions here too have a fibrous sound-absorbing or sound-insulating material or preferably a non-fibrous material as described above.

The inventive sensors can be used especially advantageously in value-document processing apparatuses. The subject of the invention is hence also a value-document processing apparatus for processing value documents with an inventive apparatus and/or inventive ultrasonic sensor. Preferably, the value-document processing apparatus has a transport device for transporting value documents to the apparatus or the ultrasonic sensor, in particular into or through the detection area of the ultrasonic sensor, and for carrying off value documents from the ultrasonic sensor, more precisely out of the detection area of the ultrasonic sensor. A processing of value documents is understood here to be in particular a check for authenticity of the value documents, for their condition, for example with regard to fitness for circulation, a sort or also a count according to number and/or value. The ultrasonic sensor can be used here in particular also for checking for double or multiple removals of value documents from a stack by a singler or for checking the condition of a value document, in particular also of the presence of a film, for example an adhesive film, on the value document.

BRIEF DESCRIPTION OF THE DRAWINGS

The invention will hereinafter be explained more closely with reference to the drawings. Therein are shown.

DETAILED DESCRIPTION OF VARIOUS EMBODIMENTS OF THE DISCLOSURE

Figure 1:
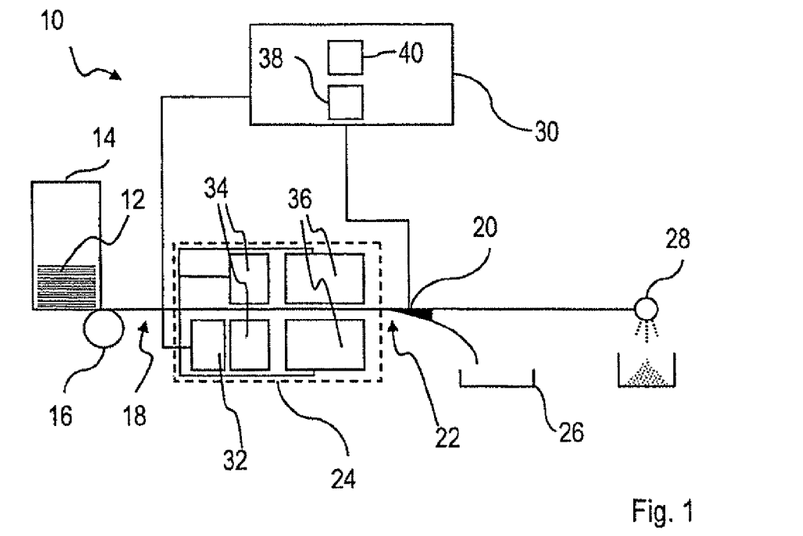
FIG. 1 a schematic representation of a bank-note processing apparatus.

FIG. 1 shows an apparatus 10 for determining a condition of value documents, in the example a bank-note processing apparatus which serves inter alia to determine the condition of value documents 12 in the form of bank notes. The apparatus 10 has an input pocket 14 for the input of value documents 12 to be processed, a singler 16 which can access value documents 12 stacked in the input pocket 14, a transport device 18 with a gate 20, and after the gate 20 an output pocket 26 and a shredder 28 for destruction of value documents or bank notes. Along a transport path 22 given by the transport device 18 there is disposed before the gate 20 and after the singler 16 a sensor assembly 24 which is used for detecting properties of singly supplied value documents 12 and forming sensor signals representing said properties. A control and evaluation device 30 is connected at least to the sensor assembly 24 and the gate 20 via signal connections and is used for evaluating sensor signals of the sensor assembly 24 and controlling at least the gate 20 in dependence on the result of evaluation of the sensor signals, i.e. of the properties of the checked value documents 12 as detected by means of the sensor assembly.

The sensor assembly 24 comprises for this purpose at least one sensor; in this exemplary embodiment there are three sensors provided, namely, a first sensor 32, in the example an optical sensor for detecting color properties which detects optical radiation reflected by the value document, a second sensor 34, in the example likewise an optical sensor for detecting special spectral security features of the value documents which detects optical radiation transmitted by the value document, and a third sensor 36, in the example an acoustic sensor, more precisely an ultrasonic sensor which detects ultrasonic signals coming from, in particular transmitted by, the value document.

Adhesive strips on the value documents 12 can be recognized for example by means of the sensor 36. For characterizing the condition of the bank notes the control and evaluation device 30 can for this purpose determine for example the number of adhesive strips or the total length or total area of the adhesive strips from the sensor signals of the sensor 36.

While a value document 12 is transported past, the sensors 32, 34 and 36 detect, according to their function, properties of scan areas on the value document determined by the position of the sensors relative to the value document, whereby the corresponding sensor signals are formed. Each of the sensors can have a different spatial resolution, i.e. the size and distribution of the detected scan areas on the value document can vary in dependence on the particular sensor and the employed transport speed. Each of the scan areas has associated therewith a place which represents the position of the scan areas for the particular sensor relative to each other and/or relative to the value document.

From the analog or digital sensor signals of the sensors 32, 34, 36 the control and evaluation device 30 determines upon a sensor signal evaluation at least one property of at least one scan area and/or at least one value-document property which are relevant for the checking of the bank notes with regard to their condition. Preferably, a plurality of said properties are determined. Further, the authenticity of the value documents is checked by means of the signals of the sensor 34. The value-document properties characterize the condition of the value documents, in this example the condition of the bank notes with regard to fitness for use or fitness for circulation, i.e. their suitability to be further employed as a means of payment. As corresponding value-document properties there are employed in this example in particular the presence of soiling or stains and the presence of tears, adhesive strips, dog's-ears and/or holes, and/or the lack of parts of the value documents. Said value-document properties can be determined in dependence on sensor signals of only one of the sensors or of at least two of the sensors.

The control and evaluation device 30 has for this purpose in particular, besides corresponding interfaces for the sensors, a processor 38 and a memory 40 connected to the processor 38 and storing at least one computer program with program code upon whose execution the processor 38 controls the apparatus or evaluates the sensor signals, in particular for determining an overall condition of a checked value document, and drives the transport device 18 in accordance with the evaluation.

In particular, the control and evaluation device 30, more precisely the processor 38 therein, can, after determination of the value-document properties, check a criterion for the overall condition of the value document which includes at least one of the value-document properties or depends on at least one of the value-document properties. The criterion can include in particular further reference data for defining a permissible condition of the value document which are predetermined and stored in the memory 40. The overall condition can be given for example by two categories, "still fit for circulation" or "fit for use", and "to be destroyed". In dependence on the determined condition, the control and evaluation device 30, in particular the processor 38 therein, controls the transport device 18, more precisely the gate 20, such that the checked value document is transported, according to its determined overall condition, for deposit to the output pocket 26 (if still fit) or for destruction to the shredder 28 (if to be destroyed).

For the processing of value documents 12, value documents 12 inserted into the input pocket 14 as a stack or singly are singled by the singler 16 and supplied singly to the transport device 18 which supplies the singled value documents 12 to the sensor assembly 24. The latter detects at least one property of the value documents 12, whereby sensor signals are formed which represent the property of the value document. The control and evaluation device 30 detects the sensor signals, determines in dependence thereon a condition of the particular value document, and drives the gate 20 in dependence on the result such that, for example, still employable value documents are supplied to the output pocket 26 and value documents to be destroyed to the shredder 28 for destruction.

For determination of the overall condition of the bank notes, the control and evaluation device 30 employs the above-mentioned criterion which can include at least one of the properties. The individual values can preferably for example be linked in a criterion, for example by means of a linear combination. The control and evaluation device 30 then, for determining the overall condition of the bank notes, compares the linear combination of the properties characterizing the condition of the bank notes to a predetermined value and decides for example whether the condition of the bank notes is good or bad, i.e. whether or not they are fit for circulation. This permits a bank note that already has considerable soiling but in isolation not enough to result in the condition of the bank note being determined as bad, to be determined as bad when the bank note additionally has e.g. only a few stains and/or tears, etc.

The ultrasonic sensor 36, an ultrasonic sensor according to a first preferred embodiment of the invention, in particular the first alternative, is partly shown more precisely in FIGS. 2 to 5.

Figure 2:
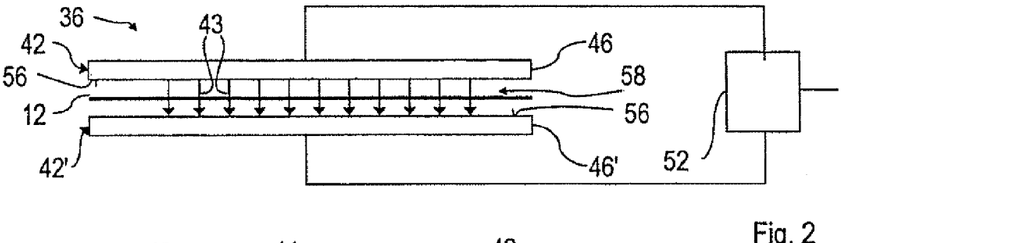
FIG. 2 a schematic side view of an ultrasonic sensor of the bank-note processing apparatus in FIG. 1, FIG. 3 a schematic plan view of a holder of the ultrasonic sensor in FIG. 2 with ultrasonic converters held therein, FIG. 4 a schematic view of a section through a portion of the holder in FIG. 3 along a plane orthogonal to a surface of the holder, FIG. 5 a schematic plan view of a molded part of a holder of a second ultrasonic sensor, FIG. 6 a schematic view of a section through a portion of the holder of the second ultrasonic sensor, FIG. 7 a schematic view of a section through a portion of a holder of a third ultrasonic sensor along a plane orthogonal to a surface of the holder, FIG. 8 a schematic plan view of a plate of the holder in FIG. 7, FIG. 9 a schematic plan view of a holder of a fourth ultrasonic sensor with ultrasonic converters held therein, FIG. 10 a schematic view of a section through the fourth ultrasonic sensor along a plane orthogonal to a surface of a holder of the ultrasonic sensor, FIG. 11 a schematic view of a section through a portion of a holder of a fifth ultrasonic sensor along a plane orthogonal to a surface of the holder, FIG. 12 a schematic plan view of a plate of the holder in FIG. 11, FIG. 13 a schematic view of a section through a portion of a holder of a sixth ultrasonic sensor along a plane orthogonal to a surface of the holder, and FIG. 14 a schematic view of a section through a seventh ultrasonic sensor along a plane orthogonal to a surface of a holder of the ultrasonic sensor.

The ultrasonic sensor 36 is provided for examining value documents 12 by means of ultrasound passing therethrough and possesses for this purpose two apparatuses 42 and 42' for emitting or receiving ultrasound in a predetermined frequency range which are identically configured according to a first preferred embodiment of the invention and except for a mirroring on a plane.

The apparatuses 42 and 42' for emitting or receiving ultrasound in the predetermined frequency range have in each case at least one, in this example eighteen, ultrasonic converters 44 for converting electrical signals into ultrasound or converting ultrasound into electrical signals, and a holder 46 or 46' in each case in which a number of ultrasonic channels 48 corresponding to the number of ultrasonic converters is formed, in the example by portions of through holes 50, in which one of the ultrasonic converters 44 is in each case disposed at least partly and through which ultrasound can pass from or to the particular ultrasonic converter 44.

The ultrasonic sensor 36 further possesses a driving and signal-processing device 52 which is connected via only schematically shown electrical connections 54 to the ultrasonic converters 44 and, not shown in FIG. 2, to the control and evaluation device 30 for the exchange of signals and supplying power.

The holders 46 and 46' are configured in a plate-like manner in their basic shape and disposed with their plate surfaces 56 parallel to each other, so that the latter are aligned in a direction orthogonal to the plate surfaces 56. The transport path 22 extends through a gap formed between the holders 46 and 46' which at the same time constitutes a detection area 58, so that value documents 12 transported through the detection area 58 can be examined by means of ultrasound in transmission. In other words, the apparatuses 42 and 42' are disposed relative to each other such that the ultrasonic converters of the apparatuses form ultrasound paths 43 when, of two ultrasonic converters 44 opposing each other in a direction orthogonal to the plate surfaces 56, one is operated as a transmitter and the other as a receiver. As illustrated in FIG. 2, the ultrasonic converters 44 are thus so disposed that the ultrasound paths 43 formed between transmitters and receiver extend in good approximation orthogonally to the value document 12 or to the plate surfaces 56.

More precisely, the ultrasonic converters 44 in the holder 46 are employed or driven as ultrasound transmitters, while the ultrasonic converters 44 in the holder 46' serve as receivers for ultrasound which has passed through a value document 12 or is radiated thereby. The ultrasonic converters serving as receivers emit corresponding detection signals upon detection of ultrasound.

The ultrasonic converters 44 are so configured in this exemplary embodiment as to be suitable for converting ultrasound with a predetermined frequency of about 400 kHz. To also permit convert of pulses with a duration smaller than 100 µs, they are preferably configured for converting ultrasound in a frequency range with a width of about 70 kHz, in the middle of which the predetermined frequency lies.

Each of the ultrasonic converters 44, which are cylindrical in the example, has a holding groove 60 along its circumference. Further, it has on its front side facing away from the detection area 58 two electrical contacts, in the example the connection wires 54, for direct or indirect electrical connection of the ultrasonic converter 44 to the driving and signal-processing device 52.

Figure 3:
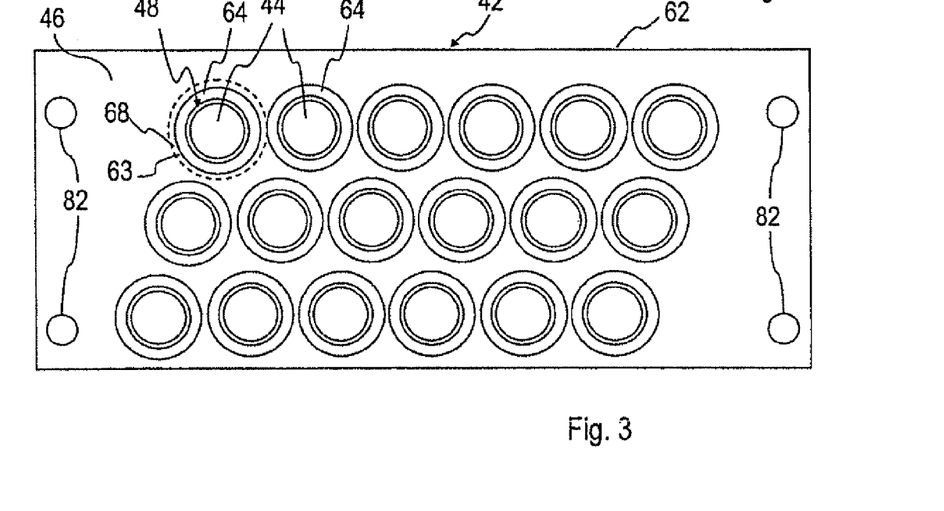
Figure 4:
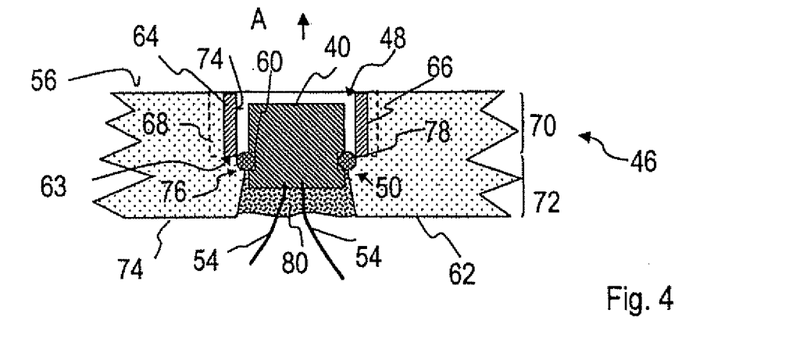

The holder 46, which, as described above, is configured like the holder 46' except for the mirroring, is shown more precisely in FIGS. 3 and 4.

The holder 46 has, firstly, a plate-shaped base body 62 in which the identically configured receiving means 63, in the example through holes, extending orthogonally to the plate surfaces 56 of the holder 46 or base body 62 are formed in three mutually offset rows at equal intervals in each case.

Secondly, the holder 46 has on a portion of the inner side of each through holes 50 or in a portion of the receiving means 63 sleeve portions or hollow cylindrical portions 64 which are formed of a different material from the base body 62. The internal spaces of the sleeve portions 64 form ultrasonic channels 48 in which ultrasound emitted or to be received by the particular ultrasonic converter can be propagated.

The base body 62 is formed in this exemplary embodiment from a glass fiber-reinforced polymer, a synthetic resin, and has a thickness of about 8 mm. The employed glass fiber-reinforced synthetic resin has a density of about $1.3 \text{ g/cm}^3$ and for the predetermined frequency an impedance of about $3 \cdot 10^6$ $\text{kg/(m}^2\text{ s)}$.

The sleeve portions 64, in contrast, are manufactured from a composite material, and thus in particular a composite material with a volume proportion of the sleeve portion 64 of more than 80%, in this exemplary embodiment a syntactic foam at least partly transmissive to ultrasound of the predetermined frequency, and form a non-fibrous surface layer 66 whose impedance is smaller than that of the base body 62 and thus of an inside layer 68 of the base body 62, and thus of the holder 46, that is neighboring to the surface layer 66, in particular adjacent thereto.

Figure 5:
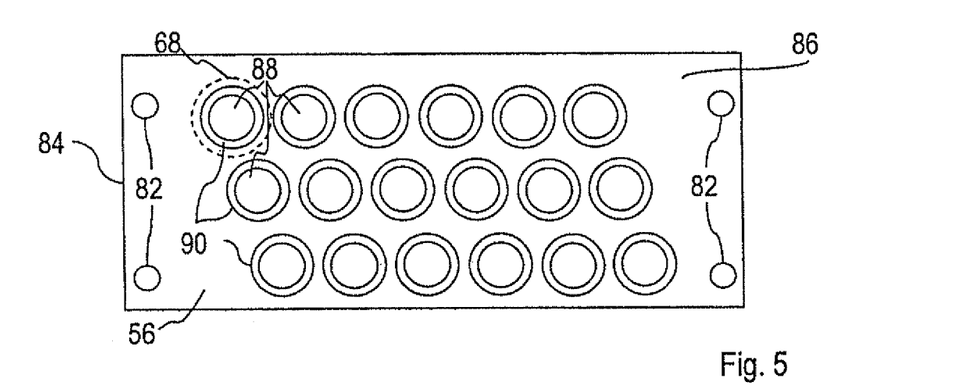

A cross section through the holder 46 in the area of one of the through holes 50 is shown schematically in FIG. 5. The other corresponding portions of the holder 46 are configured identically.

Each through hole 50 has substantially two portions 70 and 72 with different diameters, of which the portion 70, which opens on the surface 56 facing the detection area, has the greater diameter. Thus there is formed an annularly extending shoulder 76 in a middle portion on an internal surface or wall 74, forming the through hole 50, of the holder 46. Said portion 70 also comprises the sleeve portion 64.

The ultrasonic converter 44 is held via a holding element, in the example a circular ring 78, consisting of elastic, preferably sound-absorbing material which is inserted with pre-stressing into the holding groove 60, on the shoulder 76 so as to be aligned in a direction predetermined by the position of the shoulder 76 and the position of the holding groove 60 relative to the holder 46, in the example in FIGS. 2 to 5 in a direction at least approximately orthogonal to the plate surfaces 56. This results in a corresponding alignment of the receiving or transmitting characteristic (sensitivity) relative to the holder 46; the maximum and thus the radiating direction A lies approximately in a direction at least approximately orthogonal to the plate surfaces 56. Thus, with the shown arrangement of the holders 46 and 46', the transmitting and the receiving characteristics of the ultrasonic converters of a particular ultrasound path are aligned exactly with each other.

The material of the sleeve portions 64 and thus of the surface layers 66 formed thereby has a density between 0.3 g/cm$^3$ and 0.8 g/cm$^3$, preferably between 0.4 g/cm$^3$ and 0.7 g/cm$^3$.

The composite material of the sleeve portions 64 comprises a matrix with embedded bodies. In this exemplary embodiment it is, more precisely, a syntactic foam which contains in a matrix material hollow bodies, here hollow spheres, with a diameter between 5 μm and 200 μm, preferably between 5 μm and 120 μm, whereby the matrix can also contain hollow spheres of different size. The diameter distribution of the hollow spheres is so chosen that a high packing density results, although in other exemplary embodiments a monodisperse distribution can also be employed. The diameter distribution can in particular be bimodal.

In the present example, the syntactic foam contains hollow glass spheres as hollow bodies, whose diameter is preferably between 10 μm and 200 μm.

As the matrix material the syntactic foam here comprises a polymeric material, in particular a resin. In this exemplary embodiment, the polymeric material is an epoxy resin.

In this exemplary embodiment, the syntactic foam and thus the surface layer 66 possesses an average density of 0.5 g/cm$^3$, which is thus at least 10% lower than that of the inside layer 68, and a sound velocity for ultrasound of the predetermined frequency of about 2500 m/s, i.e. an impedance of about $1.3 \cdot 10^6$ kg/(m$^2$ s), which is thus between 20% and 75% of the impedance of the base body 62 and thus of the inside layer 68, in the example about 43%.

The surface layer 66 formed by the particular sleeve portion 64 hence encloses the ultrasonic channel in ring-like fashion, so that a uniform change in acoustic behavior is obtained by the surface layer. The inside layer 68 of higher impedance in turn encloses the surface layer 66.

The thickness of the surface layer 66, i.e. the wall thickness of the sleeve portion 64, is greater than one quarter of the wavelength in the surface layer 66 corresponding to the predetermined frequency and smaller than 10 mm, in this example about 1.5 mm.

Further, the sleeve portion 64 and thus the surface layer 66 extends in this exemplary embodiment in a direction orthogonal to the surface 56 or parallel to the ultrasonic channel or the radiating direction A from the surface 56 up to the holding device for the ultrasonic converter 44, here the shoulder 76.

In this exemplary embodiment, the holding groove 60 and the shoulder 76 are so configured in connection with the thickness of the holder 46 that the ultrasonic converter 44 is countersunk at least partly, in the example completely, in the ultrasonic channel 48.

The sleeve portion 64 is inserted substantially in form-fitting fashion into the receiving means 63 in the base body 62 and connected in material-locking fashion thereto. The material locking is obtained in the present example by an epoxy resin adhesive which in the cured state has an impedance that corresponds to that of the inside layer 68 and is in particular not significantly greater than that of the inside layer 68.

This configuration of the holders 46 and 46' makes it possible to obtain a strong reduction of the amplitude of singly or multiply reflected pulses or of the formation of standing waves in continuous operation.

Further, the ultrasonic converters 44 are well protected by the countersinking in the through holes 50 against mechanical action in a direction parallel to the plate surfaces.

As an optional feature, for protection of the contacting of the connecting lines 54 on the ultrasonic converter 44 from mechanical and chemical influences and for further mechanical support of the ultrasonic converter 44 in the through hole 50, the area of the through hole 50 from the ultrasonic converter 44 up to the plate surface 56 is cast with a polymeric material 80 which is electrically insulating and elastic at least to the extent that it can compensate differences in the dimensional changes of ultrasonic converters and holes caused by temperature variations. Said material is omitted in FIG. 3 for clarity's sake.

The holder 46, finally, has mounting holes 82 for fastening in the value-document processing apparatus.

A second exemplary embodiment, which at the same time constitutes a preferred embodiment according to the third alternative of the invention, differs from the first exemplary embodiment only in that the surface layers 66 are provided in a different way and the holders are modified accordingly. All the other components and features are the same as in the first exemplary embodiment, so that the same reference signs are employed therefor and the description thereof and of their function also applies here accordingly.

Figure 6:
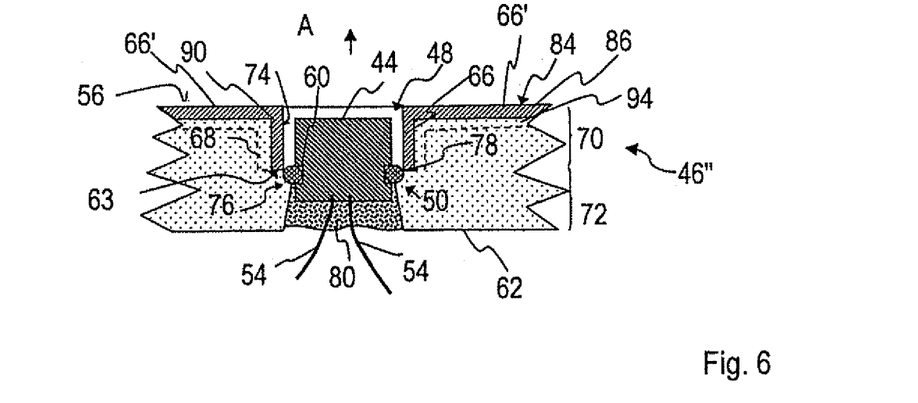

As shown schematically in FIGS. 5 and 6, a molded part 84 is now provided which is manufactured from the same material as the surface layers 66 in the first exemplary embodiment.

The molded part 84 has a plate portion 86 with through holes 88 which, when the plate portion 86 is placed accordingly on the base body 62, are flush with the through holes 50 therein. Around the through holes 88 or flush therewith there are disposed cylindrical sleeve portions 90 whose dimensions correspond to those of the sleeve portions 64 in the first exemplary embodiment. However, said sleeve portions 90 are connected integrally to the plate portion 86, so that the molded part 84 is one-pieced. In this exemplary embodiment the molded part 84 is produced by injection molding.

Said molded part 84 is inserted with the sleeve portions 90, whose internal spaces again form ultrasonic channels, into the receiving means 63 in the base body 62 and connected thereto to form a holder 46", which can be obtained for example by bonding by means of a suitable adhesive, for example, epoxy resin. In this manner there firstly result surface layers 66', corresponding to the surface layers 66 of the first exemplary embodiment, in the walls of the ultrasonic channels 48 for the ultrasonic converters 44. Secondly, the base body 62 is now covered on the side facing the detection area 58 by the plate portion 86, so that the holder 46" has on the surface 56 facing the value document 12 upon an examination a non-fibrous surface layer 92 formed by the plate portion 86 and whose impedance is smaller than that of an inside layer 94 of the holder 46" adjacent to the surface layer, which is formed by a corresponding portion of the base body 62. The impedance differences are the same as in the first exemplary embodiment.

The other holder, not shown, is constructed identically to the holder 46" except for a mirroring, as in the first exemplary embodiment. However, this need not necessarily be the case in other exemplary embodiments.

This configuration of the holders also makes it possible to avoid reflections on the surfaces of the holders and thus in the channel formed thereby, which can additionally also reduce cross-talk between neighboring ultrasound paths.

Further, the production of the sleeve portions and their assembly is facilitated, which can be a considerable advantage in particular with ultrasonic sensors having a great number of ultrasound paths.

In other exemplary embodiments it is also possible to employ syntactic foams with a different, in particular polymeric, matrix material. For example, polyurethane can also be used.

In yet other exemplary embodiments, the direction of the ultrasonic channels 48 or the principal radiating and receiving direction A of the ultrasonic converters 44 and thus of the ultrasound path can be inclined to the surface 56 and thus to a value document 12 to be examined.

Further exemplary embodiments can differ from the previously described exemplary embodiments in that instead of the through holes 50 there are provided blind holes in which the ultrasonic converters 44 are disposed at least partly.

In other exemplary embodiments, the through holes can also have holding structures on their inner side, for example projections in the form of lugs, which immediately hold the ultrasonic converters 44.

Yet other exemplary embodiments can differ from the previously described exemplary embodiments in that the sleeve portions are so configured that they serve as receiving means or holding devices for the ultrasonic converters. For this purpose, the sleeve portions can be equipped on their inner side, like the receiving means 63, with a holding structure, for example projections or a circumferential shoulder.

Furthermore, further exemplary embodiments can differ from the described exemplary embodiments in that the ultrasonic converters protrude partly out of the ultrasonic channels 48.

Further, it is possible that the base body 62 in the exemplary embodiments has at least two interconnected, in particular glued-together or mutually adherent, layers.

Figure 7:
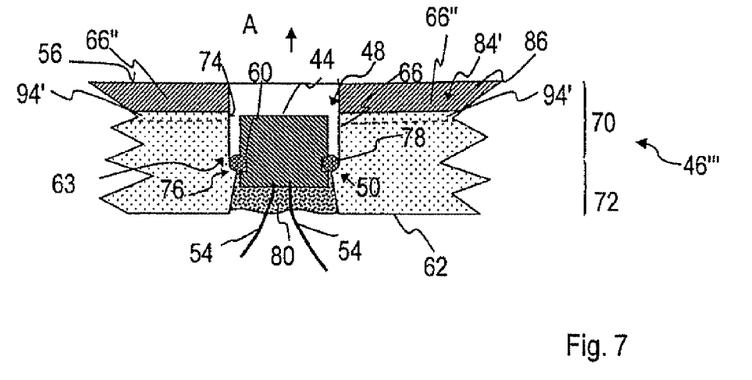
Figure 8:
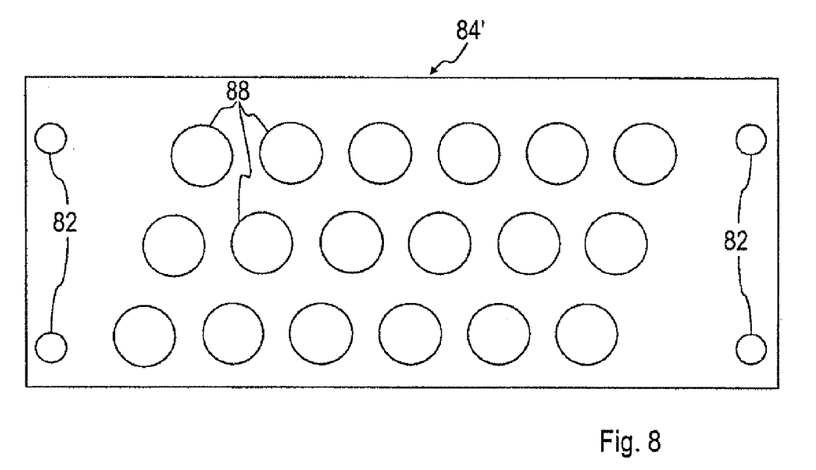

An ultrasonic sensor according to a third preferred embodiment of the invention, more precisely a preferred embodiment of the second alternative according to the invention, is illustrated schematically in FIGS. 7 and 8.

Said ultrasonic sensor differs from the ultrasonic sensor of the second exemplary embodiment only by the configuration of the holder 46'''. All the other elements of the exemplary embodiment fail to differ from the second exemplary embodiment, so that the same reference signs are employed for the same elements and the explanations thereof also hold accordingly here. The employed materials are the same as in the second exemplary embodiment.

As illustrated in FIGS. 7 and 8, the holder 46''' differs from the holder 46" firstly in that instead of the molded part 84 there is now employed a plate-shaped molded part 84' which no longer has the sleeve-like portions 90 and is hence given substantially by a plate in which there are formed, besides the holes 82, through holes 88 for forming portions of the ultrasonic channels 48. The thickness of the molded part 84 is not shown true to scale in the figures. It can be about 5 mm in the example.

Since the sleeve portions 90 are now absent, the base body 62' differs from the base body 62 in that the through holes 50 now have in the area of the portion 70 an inside diameter corresponding to that of the ultrasonic channels and thus of the through holes 88.

As illustrated in FIG. 7, the inside layer 94' of higher impedance now extends in the base body 62' parallel to the molded part 84' and thus to the non-fibrous surface layer 66" of lower impedance and approximately orthogonal to direction A of the ultrasonic channels 48 which are now adjacent to each other in direction A.

Figure 9:
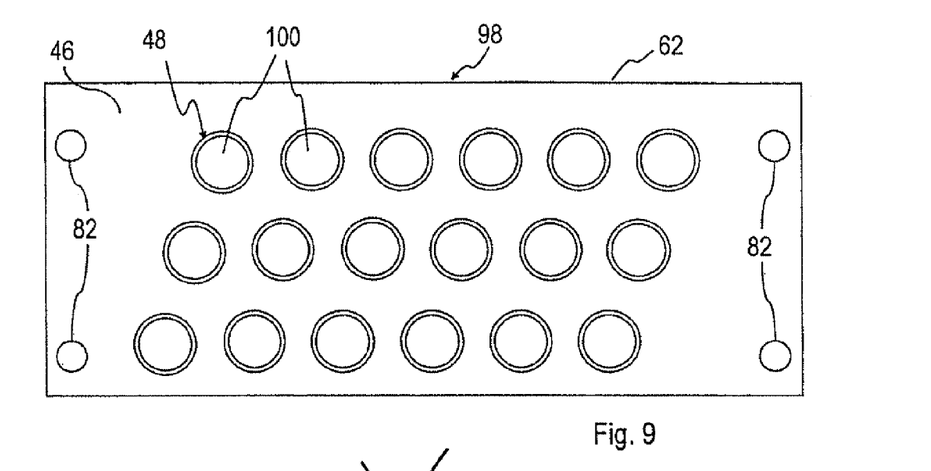
Figure 10:
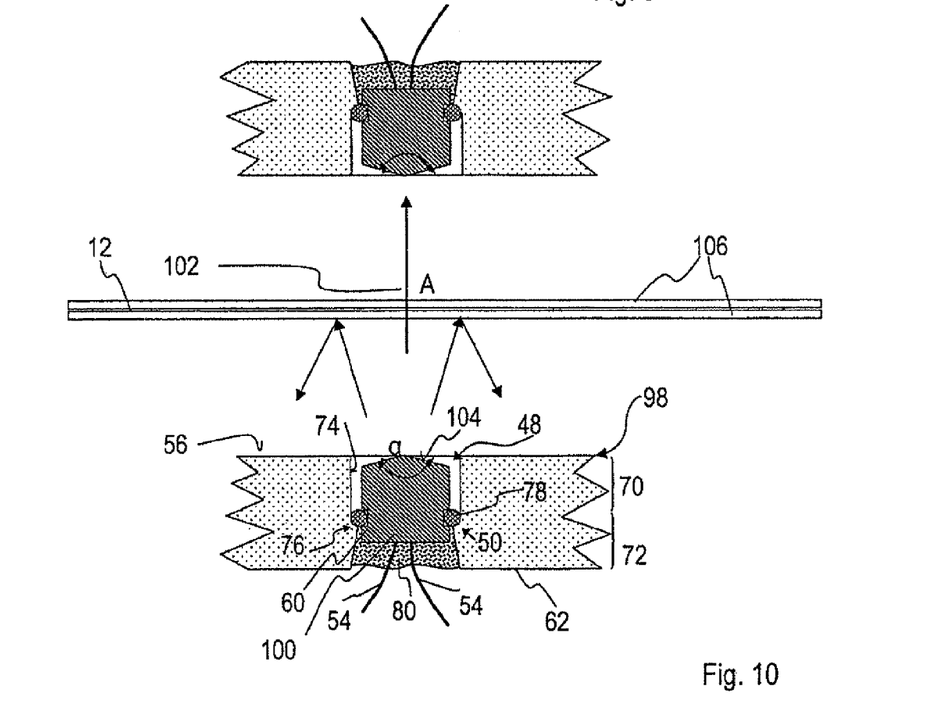

An ultrasonic sensor according to a fourth preferred embodiment of the invention, more precisely a preferred embodiment of the second alternative according to the invention, is illustrated schematically in FIGS. 9 and 10.

Said ultrasonic sensor 96 replaces the ultrasonic sensor 36 in the first exemplary embodiment. The apparatus 10 for determining a condition of value documents is otherwise unchanged.

The ultrasonic sensor 96 differs from the ultrasonic sensor 36 firstly by the use of holders 98 instead of the holders 46, 46' and secondly ultrasonic converters 100 modified compared with the ultrasonic converters 44. Otherwise the ultrasonic sensor is unchanged and thus constitutes an ultrasonic sensor for checking a value document 12 in a detection area 58 of the ultrasonic sensor by means of ultrasound at least of a predetermined frequency having an ultrasonic converter acting as a transmitter for the ultrasound and an ultrasonic converter acting as a receiver for the ultrasound, wherein the ultrasonic converters are so disposed as to form an ultrasound path 102 extending through the detection area 58. The statements on the unchanged parts and features of the ultrasonic sensor of the first exemplary embodiment apply here accordingly, and the same reference signs are employed for the same parts.

The holders 98 are changed compared with the holders 46 and 46' only to the effect that, while having the same form, they are manufactured completely from the same material, which may in particular be the material of the base body 62 in the first exemplary embodiment (cf. FIGS. 9 and 10).

The ultrasonic converters 100 are changed compared with the corresponding ultrasonic converters of the first exemplary embodiment to the effect that these have 102 inclined surface portions 104 for the radiation of ultrasound and/or for the receiving of ultrasound one relatively to the ultrasound path. This incline results firstly in the radiated ultrasound being propagated rather conically, so that portions reflected on a checked value document 12 are directed out of the area of the ultrasound path. Secondly, on the receiver side, transmitted ultrasound that is not converted by the particular ultrasonic converter is at least partly conically reflected, so that portions of the reflected ultrasound are directed out of the area of the ultrasound path 102 here too. The portions directed out of the area of the ultrasound path can no longer form standing waves or lead to pulse echoes.

Said surface portions 104 adjacent to air as the transmission medium for the ultrasound are configured to be cone-shaped or conical around the direction of the ultrasound path 102 or the radiating direction A (averaged over the beam cross section) as the axis, so that they are configured to be rotationally symmetric around the direction of the ultrasound path 102.

The cone opening angle α here is preferably between 160° and 176°, in the present example about 170°. This choice achieves a good compromise between an alignment of the radiated ultrasound, on the one hand, and a reduction of the occurrence of standing waves or of the strength of spurious pulse reflections while the amplitude of the transmitted pulses is at the same time sufficient for the checking purposes.

The surface portion 104, i.e. the conical portion, has a maximum external diameter, in a plane orthogonal to the axis of symmetry with regard to which the surface portion is rotationally symmetric, which is between the wavelength in air corresponding to the predetermined frequency and ten times the wavelength. In particular, the air can have a pressure of 1 bar, a temperature of 20° and a relative humidity of 75%. In the example the maximum external diameter is about 6 mm.

As shown in FIG. 10, the ultrasonic sensor has at least one transport element for guiding the value document 12 in the detection area 58, which in the present example is given by straps 106 between which the value document 12 is held for transport. The ultrasonic converters 100 are disposed that the ultrasound path 102 forms an angle smaller than 5° with a normal to the surface of the value document 12.

A further exemplary embodiment differs from the fourth exemplary embodiment in that the holders 98 are now replaced by the holders 46, 46' of the first exemplary embodiment or the second exemplary embodiment.

Figure 11:
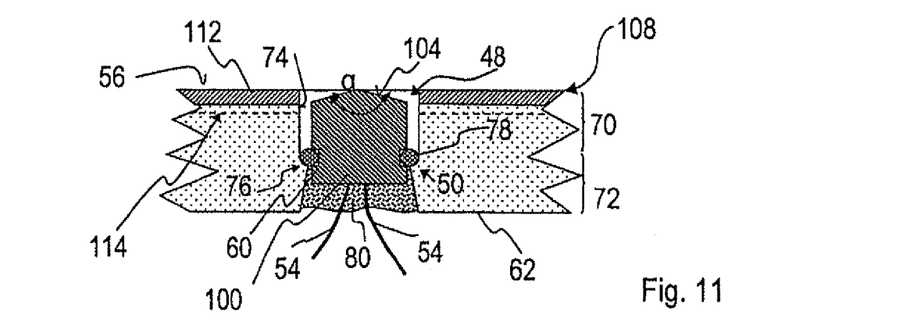
Figure 12:
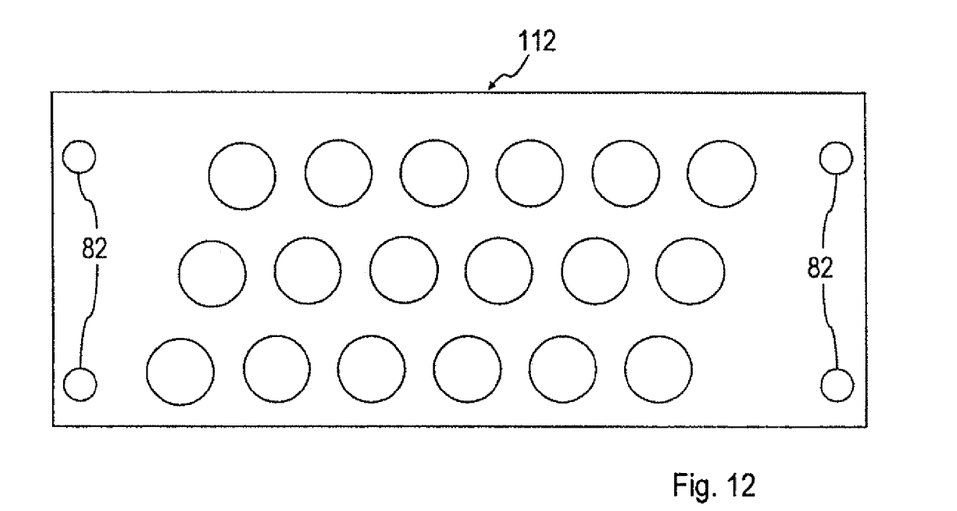
Figure 13:
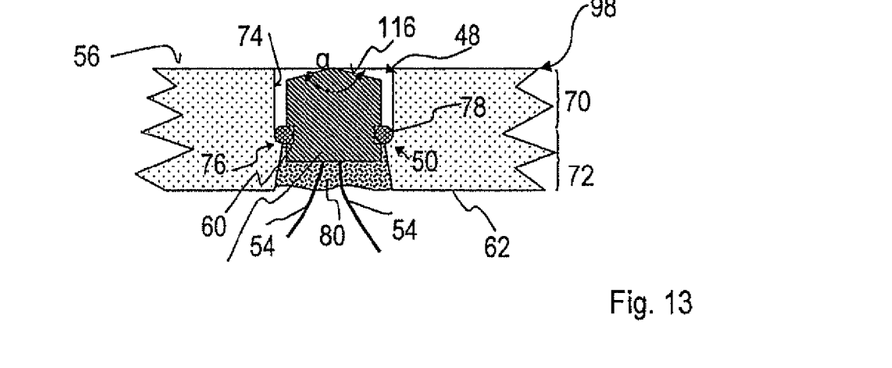

A fifth preferred embodiment of the invention in FIG. 11 and FIG. 12 differs from the fourth exemplary embodiment in that the holders 98 are replaced by holders 108. All the other parts and features of the third exemplary embodiment are unchanged, so that the same reference signs are employed therefor and the remarks thereon also apply here.

The holders 108 differ from the holders 88 only in that on a base body 110 corresponding to the holder 98 there is provided a perforated plate 112 firmly connected, for example bonded, to the base body 110 as the surface layer facing the detection area. The surface layer is constructed from a non-fibrous material whose impedance is smaller than that of the material of an inside layer 114 of the holder 108 adjacent to the surface layer. Said holder 108 forms an element limiting the detection area and absorbs at least a portion of the ultrasound impinging thereon, which additionally lowers the influence of spurious reflections.

The material of the plate 112 and thus of the surface layer formed thereby can have in particular a density between 0.3 g/cm$^3$ and 0.8 g/cm$^3$, preferably between 0.4 g/cm$^3$ and 0.7 g/cm$^3$.

In this exemplary embodiment, the material is a composite material which comprises a matrix with embedded bodies. More precisely, it is a syntactic foam which contains in a matrix material hollow bodies, here hollow spheres, with a diameter between 5 µm and 200 µm, preferably between 5 µm and 120 µm, whereby the matrix can also contain hollow spheres of different size. The diameter distribution of the hollow spheres is so chosen that a high packing density results, although in other exemplary embodiments a monodisperse distribution can also be employed. The diameter distribution can in particular be bimodal.

In the present example, the syntactic foam contains hollow glass spheres as hollow bodies, whose diameter is preferably between 10 µm and 200 µm.

As the matrix material the syntactic foam here comprises a polymeric material, in particular a resin. In this exemplary embodiment, the polymeric material is an epoxy resin.

In this exemplary embodiment, the syntactic foam and thus the surface layer possesses an average density of 0.5 g/cm$^3$, which is thus at least 10% lower than that of the inside layer 68, and a sound velocity for ultrasound of the predetermined frequency of about 2500 m/s, i.e. an impedance of about 1.3·10$^6$ kg/(m$^2$ s), which is thus between 20% and 75% of the impedance of the base body 62 and thus of the inside layer 114, in the example about 43%.

The thickness of the plate 112, i.e. of the surface layer, is greater than one quarter of the wavelength in the surface layer 112 corresponding to the predetermined frequency and smaller than 10 mm, in this example more precisely 2 mm$^2$.

This exemplary embodiment hence embodies in particular also a preferred embodiment of the third alternative of the invention, namely, ultrasonic sensor for checking a value document in a detection area of the ultrasonic sensor by means of ultrasound of a predetermined frequency having an ultrasonic converter acting as a transmitter for the ultrasound and an ultrasonic converter acting as a receiver for the ultrasound, and a holder in each case for the ultrasonic converters, wherein the holders limit the detection area, and at least one portion, limiting the detection area, of at least one of the holders has, in the surroundings of the ultrasonic converter disposed in or on the holder, a non-fibrous surface layer whose impedance is smaller than that of an inside layer of the holder adjacent to the surface layer.

In yet another exemplary embodiment, an ultrasonic converter of the first exemplary embodiment can be employed as the ultrasonic converter for receiving ultrasound.

A further exemplary embodiment differs from the fifth exemplary embodiment in that instead of the ultrasonic converters 100 there are used the ultrasonic converters 44 of the first exemplary embodiment.

A further variant of the fourth exemplary embodiment is shown in FIG. 11. It differs from the fourth exemplary embodiment only by the form of the surface portion 116, which is now also inclined to the direction of the ultrasound path and configured to be rotationally symmetric therearound. However, the surface portion 116 is lowered conically toward its center or against the radiating direction A of the ultrasound.

Figure 14:
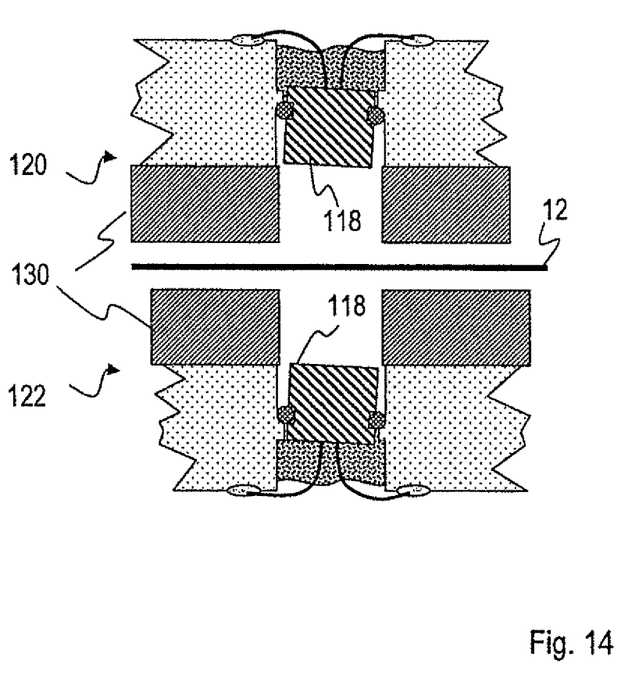

In a seventh exemplary embodiment in FIG. 14, an ultrasonic sensor has for checking a value document in a detection area of the ultrasonic sensor by means of ultrasound of a predetermined frequency having an ultrasonic converter 118 acting as a transmitter for the ultrasound and an ultrasonic converter 118 acting as a receiver for the ultrasound, a holder portion 120 and 122 in each case for the transmitter and the receiver which have ultrasonic channels flush with each other in each case in which the transmitter and receiver are so disposed in completely countersunk fashion as to form an ultrasound path extending through the detection area. The ultrasonic converters 118 are disposed so as to be inclined to an axis of alignment of the ultrasonic channels. The inclined arrangement of the ultrasonic converters relative to the ultrasound path and the ultrasonic channel forms an ultrasound path but possible echoes drift out laterally.

Particularly preferably, the surfaces of the ultrasonic channels and the surfaces of the holder portions 120 and 122 here too have a layer consisting of a fibrous sound-absorbing or sound-insulating material, for example a felt material, or preferably a non-fibrous material 130, as described above.

The invention claimed is:

1. An ultrasonic sensor for checking a value document in a detection area of the ultrasonic sensor using ultrasound of a predetermined frequency, comprising:
    an ultrasonic converter acting as a transmitter for the ultrasound and an ultrasonic converter acting as a receiver for the ultrasound;
    a holder portion in each case for the transmitter and the receiver which has an ultrasonic channel flush with each other in each case in which the transmitter and receiver are so disposed in completely countersunk fashion as to form an ultra-sound path extending through the detection area, and wherein the ultrasonic converters are disposed so as to be inclined relative to an axis of alignment of the ultrasonic channels.

2. A value-document processing apparatus for processing value documents, comprising an ultrasonic sensor according to claim 1.

3. The ultrasonic sensor according to claim 1, wherein the ultrasonic converters are configured to convert ultrasound at least of the predetermined frequency into electrical signals and/or converting electrical signals into ultrasound at least of the predetermined frequency.

4. The ultrasonic sensor according to claim 1, wherein the holder portion has at least one non-fibrous surface layer adjacent to at least one portion of the ultrasonic channels and whose impedance is smaller than that of an inside layer of the holder neighboring to the non-fibrous surface layer.

5. The ultrasonic sensor according to claim 1, wherein the holder portion has at least one surface layer that extends up to an end of the ultrasonic channel facing away from the ultrasonic converter.

6. The ultrasonic sensor according to claim 1, wherein the holder portion has at least one surface layer that encloses at least in a ring-like fashion at least the ultrasonic channel.

7. The ultrasonic sensor according to claim 1, wherein the holder comprises a base body having a receiving device and a sleeve-shaped portion disposed at least partly in the receiving device or a sleeve disposed at least partly in the receiving device, said portion or sleeve comprising a surface layer and having the ultrasonic converter disposed at least partly therein.

8. The ultrasonic sensor according to claim 1, wherein the holder portion has a surface layer formed from a material whose average density is at least 10% smaller than the average density of the material of the inside layer.

9. The ultrasonic sensor according to claim 1, wherein the holder portion has a surface layer having a density between 0.3 g/cm3 and 0.8 g/cm3.

10. The ultrasonic sensor according to claim 1, wherein the holder portion has a surface layer comprising a composite material with a weight proportion of the layer of more than 80%.

11. The ultrasonic sensor according to claim 1, wherein the holder portion has a surface layer comprising a syntactic foam.

12. The ultrasonic sensor according to claim 11, wherein the syntactic foam contains hollow bodies with a diameter between 5 µm and 200 µm.

13. The ultrasonic sensor according to claim 11, wherein the syntactic foam contains hollow glass spheres.

14. The ultrasonic sensor according to claim 11, wherein the syntactic foam contains as the matrix material a polymeric material.

15. The ultrasonic sensor according to claim 1, wherein the holder portion has a surface layer having a thickness greater than one quarter of the wavelength in the surface layer corresponding to the predetermined frequency and smaller than 10 mm.

16. The ultrasonic sensor according to claim 1, including at least one further ultrasonic con-verter, and wherein the holder includes at least one further ultrasonic channel in which the further ultrasonic converter is disposed at least partly, the holder further including at least one further non-fibrous surface layer adjacent to at least one further portion of the further ultrasonic channel, whose impedance is smaller than that of a further inside layer of the holder adjacent to the further surface layer.

17. The ultrasonic sensor according to claim 16, wherein the further surface layer extends up to an end of the further ultrasonic channel facing away from the further ultrasonic converter.

18. The ultrasonic sensor according to claim 16, wherein the surface layers for at least two of the ultrasonic channels or ultrasonic converters are formed by portions of a single molded part.

19. The ultrasonic sensor according to claim 18, wherein the holder comprises at least two layers, one of which is formed by the molded part in which the corresponding portions of the ultrasonic channels are formed.

* * * * *